United States Patent [19]
Crovetti et al.

[11] 3,932,453
[45] Jan. 13, 1976

[54] 4-NITROPYRAZOLES

[75] Inventors: Aldo Joseph Crovetti, Lake Forest; Donald Sykes Kenney, Northbrook; Don Murl Lynch, Waukegan, all of Ill.; Robert George Stein, Kenosha, Wis.

[73] Assignee: Abbott Laboratories, North Chicago, Ill.

[22] Filed: May 2, 1974

[21] Appl. No.: 466,424

Related U.S. Application Data

[62] Division of Ser. No. 282,889, Aug. 21, 1972, Pat. No. 3,869,274.

[52] U.S. Cl............................................. 260/310 R
[51] Int. Cl.²........................................ C07D 231/00
[58] Field of Search................................. 260/310 R

[56] References Cited
UNITED STATES PATENTS
3,121,092   2/1964   Geiszler.......................... 260/310 R

*Primary Examiner*—Stanley J. Friedman
*Attorney, Agent, or Firm*—Robert L. Niblack; Vincent A. Mallare

[57] ABSTRACT

Covers a method of inducing abscission of fruit by applying a chemical composition containing an effective amount of a 4-nitropyrazole as the active ingredient in an agronomically acceptable carrier. Also covers certain 4-nitropyrazoles.

8 Claims, No Drawings

4-NITROPYRAZOLES

This is a division, of application Ser. No. 282,889 filed Aug. 21, 1972 now U.S. Pat. No. 3,869,274 issued Mar. 4, 1975.

DESCRIPTION OF THE INVENTION

This invention is directed to a novel chemical method for inducing the abscission of mature to near-mature fruit from fruit-bearing plants. More specifically, this invention is concerned with a method of aiding or inducing abscission by applying a composition containing an effective amount of 4-nitropyrazole derivative having a general formula selected from the group consisting of

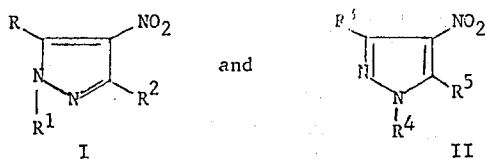

where R, $R^2$, $R^3$ and $R^5$ are selected from the group consisting of alkyl, hydrogen, halo, cycloalkyl, aryl, substituted aryl and haloalkyl; and $R^1$ and $R^4$ are selected from the group consisting of hydrogen, loweralkyl, aryl, substituted aryl, haloalkyl, halothioalkyl, arylthio, alkylthio, substituted arylthio, hydroxyalkyl, hydroxyhaloalkyl, alkylcarbamoyl, dialkylcarbamoyl, aryl substituted carbamoyl, substituted diarylcarbamoyl, alkylarylcarbamoyl, alkylsulfonyl, haloalkysulfonyl, arylsulfonyl, substituted arylsulfonyl, formyl, carboalkoxy, carboaryloxy, pyranyl, thiocarbamoyl, halocarboalkoxy, aroyl, substituted aroyl, aryloxyaceto, substituted aryloxyaceto, arylthioaceto, substituted arylthioaceto, benzyl, substituted benzyl, phenacetyl, substituted phenacetyl, phosphonoalkyl, thiophosphonoalkyl, acetylanilide and metallic salts of any of the foregoing $R^1$ and $R^4$ groups, in an agronomically acceptable carrier.

Also covers compositions containing an effective amount of at least one of the above compounds as the active ingredient in an agronomically acceptable carrier.

In addition, certain compounds having a structure falling within the formulae above are also believed to be novel. These compounds have a formulae selected from the group consisting of

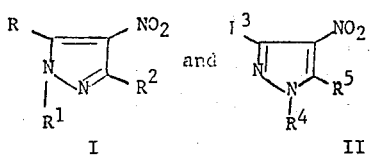

where R, $R^2$, $R^3$ and $R^5$ are selected from the group consisting of $C_2$–$C_{20}$ alkyl, hydrogen, halo, cycloalkyl, aryl, substituted aryl, and haloalkyl; and $R^1$ and $R^4$ are selected from the group consisting of hydrogen, loweralkyl, aryl, haloalkyl, halothioalkyl, arythio, alkylthio, substituted arylthio, hydroxyalkyl, hydroxyhaloalkyl, alkylcarbamoyl, dialkylcarbamoyl, aryl substituted carbamoyl, substituted diarylcarbamoyl, alkylarylcarbamoyl, alkylsulfonyl, haloalkylsulfonyl, arylsulfonyl, substituted arylsulfonyl, formyl, carboalkoxy, carboaryloxy, pyranyl, thiocarbamoyl, halocarboalkoxy, aroyl, substituted aroyl, aryloxyaceto, substituted aryloxyaceto, arylthioaceto, substituted arylthioaceto, benzyl, substituted benzyl, phenacetyl, substituted phenacetyl, phosphonoalkyl thiophosphonoalkyl, and acetylanilide, with the proviso that when $R^5$ is chloro and $R^3$ is hydrogen, the nitrogen in the one position is substituted.

The harvesting of fruit crops has traditionally been accomplished by manual labor. However, within the last several years, the shortage of manual labor prompted the development of other means for picking and harvesting fruit crops. To this end, a wide variety of mechanical devices has been developed, each of which operate in accordance with a different principle in order to remove fruit from trees or plants. For example, one device utilizes giant fans for generating strong air blasts to blow the fruit from the trees. Another device includes a series of notched or toothed arms which operate by combing the tree limbs thereby raking the fruit from the trees. Finally, mechanical shakers have been developed having an arm or boom which is connected to either a branch or the trunk of the tree and operates by violently shaking the tree in order to shake the fruit loose. However, none of these devices has been entirely successful in many crops. If the fruit is firmly attached to the tree, strong air blasts or mechanical shaking causes the fruit to strike spurs, branches and other fruit thereby bruising and damaging the fruit. Since the force necessary to remove firmly-attached fruit is usually that force necessary to tear the rind, many fruit suffer open wounds and tearing when these mechanical devices, as well as the notched arms, are used. The result is a poor quality fruit since there is usually a considerable time lapse between the time of harvesting and the time of final use within which the fruit is subject to decay where wounds and bruises appear. In addition, the force generated by these mechanical devices causes the removal of twigs, leaves and branches which are carried with the fruit to the processing plant. Such extraneous matter must be removed manually in order to avoid damage to the fruit-processing machinery, which is a time-consuming and expensive operation. Finally, it has been observed that long periods of shaking by mechanical shakers result in bark damage and disturbance to the root system, which can easily result in long-term plant destruction.

It has now been found that by first treating the fruit-bearing plants with an appropriate chemical abscission agent, the fruit are induced to abscise with either little or no mechanical aid. It is therefore one object of this invention to provide chemical compositions which will induce abscission of mature or near-mature fruit from fruit-bearing plants. Another object is to provide chemical abscission agents which operate to induce fruit abscission without causing deleterious effects to the fruit-bearing plants. Still another object is to provide a novel method for harvesting mature or near-mature fruit from fruit-bearing plants which consists essentially of applying chemical abscission agents. Another object is to provide a novel method for harvesting mature or near-mature fruit from fruit-bearing plants which combines the application of chemical abscission agents and mechanical means for complete harvesting. A further object is to provide a novel method for harvesting mature or near-mature fruit from fruit-bearing plants which combines the application of chemical abscission agents and mechanical means for complete harvesting without causing deleterious effects of the fruit-bearing plants. Other objects and advantages will be apparent to one skilled in the art upon reading this disclosure.

Fruits are generally derived from plants classified in the subkingdom Embryophyta and Pylum Angiospermae. The fruits themselves are classified as Simple fruits, Multiple fruits, and Accessory fruits. The Simple fruits include fleshy fruits, such as grapes, bananas, tomatoes and oranges, among others, and drupes such as peaches, plums, cherries and apricots. Multiple fruits are defined as a cluster of several to many ripened ovaries produced by several flowers crowded on the same inflorescence, such as osage-oranges and pineapples. Accessory fruits are those fruits having parts other than the ovaries adhering to and enclosing the mature ovaries, such as strawberries, apples, pears and quinces. The chemical method of inducing fruit abscission as disclosed herein is operative on all such types of fruits. From a practical and economic standpoint however, this invention is more concerned with the harvesting of fruit derived from fruit-bearing trees and vines having economic value, such as oranges, cherries, olives and berries, and reference will be made to this type of fruit for illustrative purposes although it is to be understood that the invention is not intended to be limited thereby.

The phenomenon of abscission or the separation of an organ, such as a leaf or fruit, from the plant is a function of biochemical reactions taking place in the organ, its stalk and the branch to which it is attached. Abscission is brought about by cellular differentiation at the base of the organ's stalk forming a cellular layer designated as the separation layer. This layer is formed from either mature cells of the stalk or as a result of growth activity in that area. The internal layer of cell walls becomes soft and gelatinous losing adherence to one another such that any slight air movement causes rupture and shedding of the organ. Although this mechanism is generally accepted, the precise biochemical pathways by which this phenomenon occurs is the subject of much speculation. Several theories have been advanced to explain this reaction mechanism, most all of which relate to changes in the concentration of the auxins or growth hormones in the organ involved. It is believed that a biochemical imbalance occurs when a fruit near ripeness, thereby causing an alteration in the auxin balance resulting in the cells at the base of the stalk forming an abscission or separation layer and causing the fruit to fall. The most current theory explains abscission as a "correlative effect in which the leaf blade or other organ (fruit) suppresses the cellular changes in which lead to separation, and this suppression involves the flow of auxin from the leaf or organ to the abscission zone. As deterioration processes set in, many materials are exported from the leaf (or organ), including some which can stimulate abscission development." (Plant Growth Development, by A. Carl Leopold, 1964, pp. 173-175).

Whatever the precise biochemical mechanism of abscission may be, it is believed that the composition disclosed herein, in some manner enter into the biochemical reactions involved in the abscission cycle in a manner to induce or hasten the abscission cycle of mature or near-mature fruit. It is the purpose of this invention, then, to disclose compositions and methods for chemically bringing about or inducing the abscission of fruit from fruit-bearing plants at the stage of fruit development just prior to full ripeness such that the fruit may be economically harvested for commercial use. Therefore, the term "abscission" as used herein refers to the separation of fruit from its stalk at the stage of development at or just prior to fruit maturity.

The above compounds are in general found by three basic schemes. In the first scheme one begins with a substituted or unsubstituted beta-keto ester and a substituted or unsubstituted hydrazine to produce a 5-pyrazolone. The 5-pyrazolones are known. Synthesis of a typical 5-pyrazolone is set out, for example, by Veibel et al, Acta. Chem. Scand. 8,768(1954). The 5-pyrazolones are then reacted with a chlorinating agent such as phosphorus oxychloride or phenyl phosphonic dichloride, to obtain the 3- or 5-chloro or 5- or 3-substituted or unsubstituted pyrazoles which are intermediates to compounds of invention. The reaction is run at a temperature ranging from 100° C to 150° C. When phenyl phosphonic dichloride is employed, reaction is run at 160°-180° C. The compounds of the invention are then formed by nitrating the just mentioned series of compounds with suitable reagents such as a mixture of nitric and sulfuric acid.

In more detail in order to synthesize one class of compounds encompassed by the invention, namely 5-chloro, 3-substituted or unsubstituted, 4-nitropyrazoles, the following procedure is employed. 0.1 mole of the 5-chloro, 3-substituted or unsubstituted intermediates were first prepared. As noted above, these were made by reacting known 5-pyrazolones with a chlorinating compound. The chlorination reaction is known and set out, for example, by Rojhm Ber 55 2959 (1922). Then 0.1 mole of the 5-chloro compound, 3-substituted or unsubstituted pyrazole will be dissolved in 100 ml of cold concentrated sulphuric acid. The solution was cooled to 10° C and 15 ml of nitric acid was added dropwise. The reaction was controlled with an ice bath to keep the reaction temperature between 20° and 25° C. After addition of the nitric acid, the solution was stirred 3 hours at room temperature and carefully poured into an ice bath. When the product crystallized, it was filtered, washed with cold water, dried and re-crystallized from various solvents. When the product is an oil, it was dissolved in ether, washed several times with water, dried, filtered and concentrated to an oil or glass and dried under high vacuo at 50°C for several hours.

Table I below lists a number of compounds prepared by the just described scheme, labeled scheme No. I

TABLE I

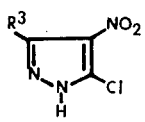

| Compound Number | R³ | Analysis Calc. Found | | | M.P. | Recrystallization Solvent | Formula |
|---|---|---|---|---|---|---|---|
| | | C | H | N | | | |
| 1 | H | | | | 183–185 | $C_2H_5OH$ | $C_3H_2ClN_3O_2$ |
| 2 | $CH_3$ | | | | 114–116 | ⬡ | $C_4H_4ClN_3O_{CIN}$ |
| 3 | $C_2H_5$ | 34.21 | 3.44 | 23.92 | 99–100 | ⬡ | $C_5H_6ClN_3O_2$ |
| | | 34.17 | 3.35 | 24.23 | | | |
| 4 | $C_3H_7$ | 38.01 | 4.25 | 22.15 | *1.5460 | — | $C_6H_8ClN_3O_2$ |
| | | 37.63 | 4.18 | 22.00 | | | |
| 5 | $i\text{-}C_3H_7$ | 38.01 | 4.25 | 22.15 | 103–105 | ⬡/Skelly B | $C_6H_8ClN_3O_2$ |
| | | 37.75 | 4.24 | 21.93 | | | |
| 6 | $t\text{-}C_4H_9$ | 41.29 | 4.95 | 20.62 | 170–172 | $C_2H_5OH$ | $C_7H_{10}ClN_3O_2$ |
| | | 41.48 | 4.95 | 21.00 | | | |
| 7 | $C_5H_{11}$ | | | 19.29 | glass | | $C_8H_{12}ClN_3O_2$ |
| | | | | 19.64 | | | |
| 8 | $C\text{-}C_6H_{11}$ | 47.07 | 5.26 | 18.28 | 133–135 | $C_2H_5OH$ $H_2O$ | $C_9H_{12}ClN_3O_2$ |
| | | 46.42 | 5.16 | 18.08 | | | |
| 9 | $C_7H_{15}$ | | | 17.09 | glass | — | $C_{10}H_{16}ClN_3O_2$ |
| | | | | 17.07 | | | |
| 10 | –⟨⟩–$NO_2$ | 40.24 | 1.87 | 21.49 | | EtOAC | $C_9H_5ClN_4O_4$ |
| | | 40.57 | 1.86 | 21.05 | | | |
| 11 | $n\text{-}C_4H_9$ | 41.29 | 4.95 | 20.62 | bp 175–180/.7 | — | $C_7H_{10}ClN_3O_2$ |
| | | 41.55 | 5.01 | 20.94 | $n_D^{25}$ 1.5412 | | |

*Refractive index - $n_D^{25}$

In yet another scheme, a series of N-substituted pyrazoles were prepared. Here the same reaction scheme was followed as scheme I with the exception that the hydrazines employed to form the 5-pyrazolones were in all substances substituted hydrazines. In some instances, mixtures were obtained where the N-substitutions were obtained on both the one or two position nitrogen atom. In other cases, even where pure compounds were formed it was impossible to determine by analytical methods whether the N-substituent was on the one or two position, that is being either $R^1$ to give structure I or $R^4$ to give structure II. In yet other instances, pure compounds were obtained where it could be determined on which particular nitrogen atom the substitution took place. Specifically, with respect to compound Numbers 14, 15, 16, 17 and 18 described below, 1-substituted pyrazoles were obtained. In an alternate route the 3-methyl, 4-nitro, 5-chloro pyrazole was reacted with an appropriate alkylating or acylating agent.

Table II below summarizes physical characteristics of the compounds prepared according to scheme II.

TABLE II

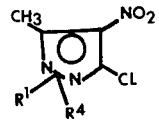

| Compound Number | $R^1$ or $R^4$ | Analysis Calc. Found | | | M.P. | Recrystallization Solvent | Formula |
|---|---|---|---|---|---|---|---|
| | | C | H | N | | | |
| 12 | H | | | | 108–110 | ⬡ | $C_4H_4ClN_3O_2$ |
| 13 | $CH_3$ | | | | 77–78 | ⬡ | $C_5H_6ClN_3O_2$ |
| 14 | $CH_2OH$ | 31.35 | 3.16 | 21.93 | 111–112 | ⬡ | $C_5H_6ClN_3O_3$ |
| | | 31.47 | 3.18 | 22.26 | | | |
| 15 | $CH_2Cl$ | 28.59 | 2.40 | 20.01 | 72–4.5 | ⬡/Skelly B | $C_5H_5Cl_2N_3O_2$ |
| | | 28.86 | 2.50 | 20.27 | | | |
| 16 | $C_3H_7$ | 41.16 | 4.69 | 20.55 | 12–14 | | $C_7H_{10}ClN_3O_2$ |
| | | 41.33 | 5.06 | 20.44 | | | |
| 17 | $C_2H_4Cl$ | 32.16 | 3.15 | 18.76 | 66–68 | | $C_6H_7Cl_2N_3O_2$ |
| | | 32.35 | 3.08 | 18.85 | | | |

TABLE II-continued

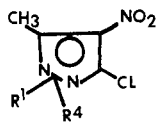

| Compound Number | R¹ or R⁴ | C | Analysis H Calc. Found | N | M.P. | Recrystallization Solvent | Formula |
|---|---|---|---|---|---|---|---|
| 18 | —⌬ | 50.50 / 50.21 | 3.39 / 3.22 | 17.64 / 17.76 | 113–115 | $C_2H_5OH$ | $C_{10}H_8ClN_3O_2$ |
| 19 | —⌬—NO₂ | | | | 180–182 | $C_2H_5OH$ | $C_{10}H_7ClN_5O_3$ |
| 20 | ‖O C—CH₃ | 35.40 / 35.24 | 2.97 / 2.93 | 20.64 / 20.83 | 73–76 | Skelly B | $C_6H_6ClN_3O_3$ |
| 21 | ‖O C—CH₂Cl | 30.27 / 30.31 | 2.12 / 2.12 | 17.65 / 17.93 | 91–94 | ⌬ | $C_6H_5Cl_2N_3O_3$ |
| 22 | ‖O C—⌬ | 49.73 / 49.66 | 3.04 / 2.93 | 15.82 / 15.69 | 97.5–100 | ⌬ / Skelly B | $C_{11}H_8ClN_3O_3$ |
| 23 | ‖O C—NHCH₃ | 32.96 / 32.67 | 3.23 / 3.06 | 25.63 / 25.83 | 126–130 | ☐ | $C_6H_7ClN_4O_3$ |
| 24 | ‖O C—N(CH₃)₂ | 36.14 / 36.49 | 3.90 / 3.85 | 24.09 / 23.95 | | ⌬ / Skelly B | $C_7H_9ClN_4O_3$ |
| 25 | ‖O CNH—⌬ | 47.07 / 47.05 | 3.23 / 3.21 | 19.96 / 20.10 | 143–146 | ☐ | $C_{11}H_9ClN_4O_3$ |
| 26 | ‖O CNH—⌬—Cl | 41.93 / 42.02 | 2.56 / 2.49 | 17.78 / 17.86 | 151–153 | ⌬ | $C_{11}H_8Cl_2N_4O_3$ |
| 27 | ‖O CNH—⌬(Cl)—Cl | 37.79 / 37.96 | 2.02 / 1.99 | 16.03 / 16.43 | 178–181 | ☐ | $C_{11}H_7Cl_3N_4O_3$ |
| 28 | ‖O C—O—C₂H₅ | 35.99 / 36.21 | 3.45 / 3.43 | 17.99 / 18.31 | 93–96 | ⌬ / Skelly B | $C_7H_8ClN_3O_4$ |
| 29 | —O₂SCH₃ | 25.06 / 25.21 | 2.52 / 2.56 | 17.54 / 17.64 | 111–112.5 | EtOH | $C_5H_6ClN_3O_4$ |
| 30 | O₂S—⌬—CH₃ | 41.84 / 41.59 | 3.19 / 3.21 | 13.31 / 13.45 | 148–150 | CCl₄ | $C_{11}H_{10}ClN_3O_4S$ |
| 31 | SCCl₃ | 19.37 / 19.50 | .97 / .98 | 13.50 / 13.72 | 63–64 | ⟨S⟩ | $C_5H_3Cl_4N_3O_2S$ |
| 32 | —⟨O⟩ | 44.00 / 43.97 | 4.92 / 5.04 | 17.09 / 17.27 | 60–62 | ⟨S⟩ | $C_9H_{12}ClN_3O_2$ |
| 33 | ‖O C—OCH₃ | 32.82 / 33.18 | 2.75 / 2.77 | 19.14 / 19.44 | 71–72 | Skelly B / ⌬ | $C_6H_6ClN_3O_4$ |
| 34 | ‖O CCH₂O—⌬ | 48.74 / 48.80 | 3.41 / 3.40 | 14.21 / 14.33 | 184–187 | ⌬ | $C_{12}H_{10}ClN_3O_4$ |
| 35 | —CCH₂O—⌬(Cl)—Cl ‖O | 39.53 / 39.83 | 2.21 / 2.22 | 11.53 / 11.64 | 172–174 | CHCl₃ | $C_{12}H_8Cl_3N_3O_4$ |
| 36 | ‖O O—⌬(Cl)—Cl | 39.49 / 39.76 | 1.81 / 1.81 | 12.56 / 12.77 | 159–162 | CH₃CN | $C_{11}H_6Cl_3N_3O_3$ |
| 37 | ‖O C—C(CH₃)₃ | 44.00 / 44.14 | 4.93 / 5.01 | 17.10 / 17.42 | 77–80 | ⌬ / Skelly B | $C_9H_{12}ClN_3O_3$ |

The following examples illustrate preparation of typical compounds of the invention by means of reaction scheme II.

COMPOUND NO. 14

N-Hydroxymethyl-3-chloro-5-methyl-4-nitropyrazole

A solution of 10.0 g (0.0619 mole) of 3(5)-methyl-4-nitro-5(3)-chloro pyrazole in 12.05 ml of 37% formaldehyde and 13.78 ml (16.8 g, 0.365 mole) of formic acid was heated under reflux by means of a steam bath for 16 hours. The solution was cooled in an ice bath and 9.28 ml of concentrated hydrochloric acid was added. Heating in the steam bath was continued for 5 hours. This solution was cooled and poured onto ice. The mixture was filtered and the solid was washed with water and dried in vacuo at room temperature to yield 10.18 g of a faint yellow solid. The solid was dissolved in boiling benzene and filtered hot. From the filtrate there separated out 7.74 g of light yellow crystals.

COMPOUND NO. 15

3-chloro-N-chloromethyl-5-methyl-4-nitropyrazole

A mixture of 13.58 g (0.0708 mole) 1-hydroxymethyl-3-chloro-5-methyl-4-nitropyrazole and 30 ml of thionyl chloride was heated under reflux overnight and concentrated in vacuo. Benzene was added and the solution was concentrated again. This was replicated two more times. This left 15.8 g of an amber liquid. This was distilled at 155°–170° (air bath temperature)/1.25 mm to obtain a colorless liquid which crystallized upon standing. Recrystallization from benzene-Skelly B solvent gave 9.52 g of white crystals.

COMPOUND NO. 16

5-chloro-3-methyl-4-nitro-1-propylpyrazole 102 g (0.644 mole) of 5-chloro-3-methyl-1-n-propylpyrazole was added with stirring to 175 ml of concentrated sulfuric acid, keeping the temperature below 30°C. To this was then added 130 ml of fuming nitric acid and the resultant mixture was stirred about an hour at less than 30°C. The product was poured over ice and a light yellow oil formed. This was extracted with benzene, and then the benzene layer was washed with potassium hydroxide solution and then water for three successive times. The benzene was then distilled at atmospheric pressure to obtain a residual oil. The oil was then distilled to obtain the product.

In order to provide the 5-chloro-3-methyl-1-n-propylpyrazole product, the following procedure was followed: 160 g (1.14 mole) of 3-methyl-1-n-propyl-5-pyrazolone was added to 600 ml of phosphorus oxychloride and, the mixture was refluxed together for 3 hours. The excess phosphorus oxychloride was then distilled with a packed column. The residual dark oil was poured over ice and an acidic solution resulted. This was made strongly alkaline with concentrated potassium hydroxide solution and then continuously extracted with benzene for 16 hours. The aqueous solution was neutral and was again made alkaline with potassium hydroxide and extracted in portions with benzene. The combined benzene extracts were concentrated by distillation at atmospheric pressure. The residue contained a fine solid which was filtered and then distilled in vacuo to obtain the desired product.

COMPOUND NO. 17

5-chloro-1-(beta-chloroethyl)-3-methyl-4-nitropyrazole 3.6 g (0.02 mole) of 5-chloro-1(beta-chloroethyl)-3-methylpyrazole was added slowly to 10 ml of concentrated sulfuric acid with swirling. Thereafter 5 ml of fuming nitric acid was then added slowly also with swirling. During the addition, the mixture became quite warm. It was allowed to stand at room temperature for 40 minutes and then poured onto ice. A white solid was formed and was filtered off, washed well with water and dried in vacuo at 56°C.

COMPOUND NO. 18

5-chloro-3-methyl-1-phenyl-4-nitropyrazole

A solution of 9.6 g (0.05 mole) of 5-chloro-3-methyl-1-phenylpyrazole and 25 ml of acetic anhydride was added at 10°C to a solution of acetyl nitrate prepared from 25 ml of 90% nitric acid and 10 ml of acetic anhydride. The solution was stirred 2 hours at 20°–30°C and carefully poured onto ice water. The solid was filtered off and washed with cold water. One recrystallization from ethanol gave long white needles of product.

COMPOUND NO. 20

N-Acetyl-3(5)-chloro-5(3)-methyl-4-nitropyrazole

A solution of 10.0 g (0.0619 mole) of 3(5)-methyl-4-nitro-5(3)-chloropyrazole and 30 ml of acetic anhydride was stirred and heated at 110°–115°C for 3 hours. The solution was concentrated in vacuo at 65°–70°C to yield 15.6 g of a tan solid. Crystallization from Skelly B afforded 8.82 g of very light amber crystals. The crystals were dissolved in hot Skelly B and filtered hot. From the filtrate there separated 7.15 g of white crystals.

COMPOUND NO. 21

3(5)-chloro-N-chloroacetyl-5(3)-methyl-4-nitropyrazole

A solution of 10 g (0.0619 mole) of 3(5)-methyl-4-nitro-5(3)-chloropyrazole in 30 ml (44.9 g, 0.398 mole) of chloroacetylchloride was stirred and heated under reflux for 3½ hours. This solution was concentrated in vacuo at 50°C to yield 19.18 g of amber liquid that crystallized upon standing. Crystallization from benzene-Skelly B gave 12.41 g of amber crystals. Recrystallization from benzene yielded 6.57 g of crystals.

COMPOUND NO. 22

N-benzoyl-3(5)-chloro-5(3)-methyl-4-nitropyrazole

To a stirred mixture of 10 g (0.0619 mole) 3(5)-methyl-4-nitro-5(3)-chloropyrazole, 100 ml of benzene and 7.25 ml of benzoyl chloride was added drop-wise for 10 minutes, 4.98 ml (4.9 g, 0.0619 moles) of pyridine in 50 ml of benzene. The mixture was stirred at room temperature for 3 hours and filtered with suction. The filtrate was concentrated in vacuo to yield 14.92 g of a mixture of solid and liquid. The mixture was warmed in a small amount of benzene and allowed to cool and then filtered. The filtrate was concentrated in vacuo to yield 13.67 g of a tan solid. This was taken up in warm benzene and filtered warm. Upon cooling, the mixture was filtered again and Skelly B was added to the filtrate, yielding 7.56 g of beige crystals.

COMPOUND NO. 24

3(5)-chloro-N-dimethylcarbamyl-5(3)-methyl-4-nitropyrazole

To a stirred mixture of 10 g (0.0619 mole) 3(5)-methyl-4-nitro-5(3)-chloropyrazole, 100 ml of benzene and 5.74 ml (6.72 g, 0.0625 mole) of dimethylcarbamyl chloride was added rapidly 4.98 ml (4.9 g, 0.0619 mole) of pyridine in 50 ml of benzene. This solution was heated under reflux for 6 hours, allowed to cool and filtered with suction. The filtrate was concentrated in vacuo to yield 14.88 g of an amber liquid that slowly solidified upon standing. The product was then stirred in 200 ml of benzene and benzene decanted from the amber oil. Concentration of the benzene in vacuo left 9.59 g of a yellow solid. Crystallization from benzene-Skelly B provided 5.35 g of cream colored crystals. Recrystallization from benzene yielded 1.98 g of product.

COMPOUND NO. 25

3(5)-chloro-5(3)-methyl-4-nitro-N-carbanilinopyrazole

A mixture of 10.00 g (0.0619 mole) of 3(5)-methyl-4-nitro-5(3)-chloropyrazole and 6.73 ml (7.37 g, 0.0619 mole) of phenylisocyanate in 250 ml of benzene was stirred and heated under reflux for 4 hours. The reaction mixture was filtered hot from a small amount of dark solid and allowed to cool. The solution was concentrated in vacuo and a white solid residue was recrystallized from benzene to yield 12.13 of white crystals. Recrystallization from benzene yielded 9.3 g of crystals. A second recrystallization from dioxane yielded 7.95 g of crystals.

COMPOUND NO. 26

3(5)-chloro-5(3)-methyl-4-nitro-N-carb-(p-chloroanilino)-pyrazole

A mixture of 10.00 g (0.0619 mole) of 3(5)-methyl-4-nitro-5(3)-chloropyrazole and 9.59 g (0.0625 mole) of p-chlorophenylisocyanate in 250 ml of benzene was stirred and heated under reflux for 4 hours and allowed to cool to room temperature. The mixture was filtered by suction to yield 14.18 of beige colored solid. Recrystallization from benzene afforded 11.8 g of product.

COMPOUND NO. 27

3(5)-chloro-5(3)-methyl-4-nitro-N-3,4-dichlorophenylcarbamyl pyrazole

A mixture of 10.00 g (0.0619 mole) of 3(5)-methyl-4-nitro-5(3)-chloropyrazole, 11.75 g (0.0625 mole) of 3,4-dichlorophenyl isocyanate in 250 ml of benzene was stirred and heated under reflux for 4 hours. The mixture was allowed to cool and filtered with suction to give 17.01 g of cream colored solid. The solid was dissolved in hot dioxane, and filtered hot. From the filtrate there separated out 14.32 g of beige crystals.

COMPOUND NO. 28

5(3)-methyl-4-nitro-(3(5)-chloro-N-carbethoxypyrazole

To a mixture of 10.00 g (0.0619 mole) of 3(5)-methyl-4-nitro-5(3)-chloropyrazole and 70 ml of benzene was added 5.97 ml (6.78 g, 0.0625 mole) of ethyl chloroformate followed by 4.98 ml (4.9 g, 0.0619 mole) of pyridine. The mixture was stirred and heated under reflux for 2 hours and 15 minutes and then filtered by suction. The solid was washed with benzene and weighed dry 6.31 g. From the filtrate upon cooling, there separated 0.9 g of white crystals. The filtrate from the solid material was concentrated in vacuo to yield 13.58 g of a cream colored solid. The solid was taken up in a minimum amount of warm benzene and filtered warm from a trace of insoluble material. Skelly B was added to the filtrate to give 11.8 g of white crystals.

COMPOUND NO. 29

3(5)-chloro-N-methanesulfonyl-5(3)-methyl-4-nitropyrazole

To an ice cooled solution of 10 g (0.0619 mole) of 3(5)-methyl-4-nitro-5(3)-chloropyrazole in 140 ml of pyridine was added 8.73 ml (12.92 g, 0.124 mole) of methanesulfonyl chloride. The solution was kept at 5°C for 24 hours, and poured into ice. Filtration gave 6.88 g of amber solid. This was dissolved in boiling ethanol and filtered hot. From the filtrate there separated 5.15 g of brown crystals.

COMPOUND NO. 30

3(5)-chloro-5(3)-methyl-4-nitro-N-(p-toluenesulfonyl) pyrazole

To an ice cooled solution of 17.7 g (0.1097 mole) OF 3(5)-methyl-4-nitro-5(3)-chloropyrazole in 250 ml of pyridine was added 41.7 g (0.2194 mole) of p-toluenesulfonyl chloride. The mixture was swirled in the ice bath until solution was complete and then held at 5°C for 24 hours, and thereafter poured onto ice. The mixture was filtered with suction and the solid was washed well with water. The damp solid was taken up in boiling ethanol but would not dissolve. The liquid was allowed to cool and filtered with suction. This gave 20.01 g of dull white solid. The solid was taken up in boiling carbon tetrachloride and filtered hot. From the filtrate separated 14.91 g of dull white crystals.

COMPOUND NO. 31

3(5)-chloro-5(3)-methyl-4-nitro-N-(trichloromethylmercapto)-pyrazole 9.25 g (0.05 mole) of trichloromethylsulfonyl chloride was added drop-wise to an ice cooled stirred solution of 8.05 g (0.05 mole) of 3(5)-chloro-5(3)-methyl-4-nitropyrazole, 2 g (0.05 mole) sodium hydroxide in 100 ml of water. The mixture was stirred 1 hour and then filtered. The filtered cake was dissolved in ether, washed with water, dried over magnesium sulfate, filtered and concentrated in vacuo to give a low melting solid. Recrystallization from Skelly B gave a 5.7 g of product.

COMPOUND NO. 32

3(5)-chloro-5(3)-methyl-4-nitro-N-(tetrahydro-2-H-pyran-2-yl)pyrazole

A solution of 16.1 g (0.10 mole) of 3(5)-chloro-5(3)-methyl-4-nitropyrazole, 10 ml of dihydropyran, 0.2 g of p-toluenesulfonic acid and 200 ml of benzene was stirred at room temperature for 12 hours. The solution was washed with 5% sodium hydroxide, followed by a wash water. The benzene solution was dried over magnesium sulfate, filtered and concentrated in vacuo to give a tan solid. One recrystallization from cyclohexane gave 14.8 g of product.

COMPOUND NO. 33

3(5)-chloro-5(3)-methyl-4-nitro-N-carbomethoxypyrazole

To a stirred mixture of 10 g (0.0619 mole) of 3(5)-methyl-4-nitro-5(3)-chloropyrazole, 100 ml of benzene and 4.78 ml (5.91 g, 0.0625 mole) of methyl chloroformate was added drop-wise over 15 minutes 4.98 ml (4.9 g, 0.0619 mole) of pyridine in 50 ml of benzene. The mixture was stirred at room temperature for 2 hours and 45 minutes and filtered with suction. The filtrate was concentrated in vacuo to yield 11.5 g of cream colored solid. The solid was taken up in a small amount of warm benzene, allowed to cool and filtered. Skelly B was added to the filtrate affording 8.67 g of beige crystals.

COMPOUND NO. 34

3(5)-chloro-5(3)-methyl-4-nitro-N-phenoxyacetyl-pyrazole

To a stirred mixture of 10 g (0.0619 mole) of of 5(3)-chloro-3(5)-methyl-4-nitropyrazole, 100 ml of benzene and 10.66 g (0.0625 mole) of phenoxyacetyl chloride was added dropwise over 15 minutes 4.98 ml (4.9 g, 0.0619 mole) of pyridine in 50 ml of benzene. The mixture was stirred at room temperature for 3 hours and filtered with suction. The filtrate was concentrated in vacuo to yield 3.29 g of white solid. Recrystallization from benzene afforded 1.41 g of product. The insoluble material from the first filtration was also taken up in boiling benzene and filtered hot. From the filtrate there separated 3.37 g of white crystals.

COMPOUND NO. 35

3(5)-chloro-N-(2,4-dichlorophenoxyacetyl)-5(3)-methyl-4-nitropyrazole

To a stirred mixture of 10 g (0.0619 mole) of 3(5)-methyl-4-nitro-5(3)-chloropyrazole and 150 ml of benzene was added 14.97 g (0.0625 mole) of 2,4-dichlorophenoxyacetyl chloride followed by 4.98 ml (4.9 g, 0.0619 mole) of pyridine in 50 ml of benzene dropwise over 15 minutes. The mixture was stirred at room temperature for 3 hours, heated to reflux and filtered with suction. The filtrate was concentrated in vacuo and the residue was taken up in a small amount of benzene and filtered hot. The filtrate crystallized immediately. It was reheated and filtered again. The process was again repeated and the filtrate was allowed to cool and filtered with suction. This gave 21.33 g of white crystals. The crystals were dissolved in boiling chloroform and filtered hot with slight suction. From the filtrate there separated 9.78 g of white crystals.

COMPOUND NO. 37

3(5)-chloro-5(3)-methyl-N-trimethylacetyl-4-nitropyrazole

To a stirred mixture of 10 g (0.0619 mole) of 3(5)-methyl-4-nitro-5(-3)-chloropyrazole, 150 ml of benzene, and 7.53 g (0.0625 mole) of pivalyl chloride was added dropwise over 10 minutes 4.98 ml (4.9 g 0.0619 mole) of pyridine and 50 ml of benzene. The mixture was stirred at room temperature for 3 hours and filtered with suction. The filtrate was concentrated in vacuo to yield 9.43 g of beige solid. This was taken up in boiling benzene but would not dissolve. The mixture was allowed to cool and filtered with suction (1.08 g of insoluble beige solid). The filtrate was concentrated in vacuo, taken up in a small amount of boiling benzene, cooled and filtered to remove a small amount of material. The filtrate was diluted with Skelly B and placed in a cold room over night. This gave 1.2 g of white crystals. Filtrate from the 1.2 g solid was concentrated in vacuo and the residue was crystallized from Skelly B to give 1.7 g of product. The filtrate from the 1.7 g solid product was cooled in ice, giving 0.62 g of product.

In scheme III, known compounds were employed as starting material and nitrated in the manner set out above. Table III outlines the physical characteristics of these products.

TABLE III

| Compound Number | R⁵ | C Calc. Found | H Calc. Found | N Calc. Found | M.P. | Recrystallization Solvent | Formula |
|---|---|---|---|---|---|---|---|
| 38 | H | | | | 132–134 | H$_2$O | C$_4$H$_5$N$_3$O$_2$ |
| 39 | Br | 23.31 / 23.46 | 1.95 / 1.95 | 20.38 / 20.49 | 143–144 | EtOAC | C$_4$H$_4$BrN$_3$O$_2$ |
| 40 | CH$_3$ | | | | 127–128 | H$_2$O | C$_5$H$_7$N$_3$O$_2$ |
| 41 | CF$_3$ | 30.78 / 30.56 | 2.07 / 2.03 | 21.54 / 21.40 | Oil | — | C$_5$H$_4$F$_3$N$_3$O$_2$ |

Representative compounds of Table III were prepared as follows:

COMPOUND NO. 41

5-bromo-3-methyl-4-nitropyrazole 6.5 g (0.027 mole) of 4,5-dibromo-3-methylpyrazole was dissolved in 20 ml of concentrated sulfuric acid. The solution was cooled to 9°C and 10 ml of 90% nitric acid was added dropwise. The solution was stirred 30 minutes and then slowly heated to 60°C and kept at that temperature for 30 minutes. The solution was cooled and poured into water. The mixture was extracted with ether and the ether was washed with water. The ether solution, after drying over magnesium sulfate was concentrated in vacuo and gave a white solid (1.5 g). One recrystallization from ethyl acetate gave a solid product.

COMPOUND NO. 41

3(5)-trifluoromethyl-5(3)-methyl-4-nitropyrazole

To obtain the starting material necessary to achieve the final product, 3(5)-trifluoromethyl-5(3)-methylpyrazole, the following reaction was first run: To a stirred mixture of 30.8 g (0.2 mole) of trifluoroacetylacetone in 150 ml of water was added dropwise over 20 minutes, 14.0 g (0.28 mole) of hydrazine hydrate. The mixture was stirred and then heated on a steambath for 1 hour, cooled and filtered with suction. The solid was washed with water and air dried, giving 23.61 g of dull yellow solid. Crystallization from Skelly B at 0°C gave 19.17 g of amber colored crystals.

10.0 g (0.0666 mole) of 3(5)-trifluoromethyl-5(3)-methylpyrazole was dissolved portionwise in 14.4 ml of concentrated sulfuric acid with cooling. The time of addition was approximately 25 minutes and the temperature was kept below 20°C. 7.77 ml of 90% nitric acid was added dropwise to the ice cold solution over a period of 30 minutes. The mixture was stirred at room temperature for 2 hours and then heated in a boiling water bath for 30 minutes, cooled and poured onto ice. This gave a mixture of solid and liquid. The mixture was extracted with ether. The ether extract was washed with water and then dried over magnesium sulfate. Removal of the solvent left 13.13 g of a yellow liquid.

Suitable abscission agents must fulfill two basic requirements: First, they must enter into the biochemical abscission mechanism and induce or hasten the separation of mature or near-mature fruit from its stem; and second, these agents must induce abscission without at the same time exhibiting severe phytotoxic properties. At the present time, there are a few known chemical compounds which have the demonstrated ability to induce or hasten fruit abscission, such as iodoacetic acid, ethylene, and allyl alcohol, the most successful agent being iodoacetic acid. However, iodoacetic acid (hereinafter referred to as IOAA) as well as the few other agents known in the art are decidedly phytotoxic. For example, IOAA will cause leaf burn at a concentration of 100 parts per million (ppm) and at higher concentrations, extensive phytotoxicity is very prevalent.

The compounds disclosed herein, on the other hand, exhibit abscission activity and are at the same time, non-phytotoxic at the effective level. Furthermore, it appears to be of no significance whether the compounds are applied topically as by spraying the plants or trees, or by dispersing them in the ground for transmission to the organs through the stems.

The foregoing compounds were tested for their activity as abscission agents by two methods. The first method involved treatment of Calomondin trees. The following procedure was followed: First the compounds were solubilized. Here, 150 mg of a compound was weighed into a plastic bottle that was compatible with the hand sprayer used. After weighing the compound, 10 ml of an isopropyl alcohol-Tween 20 mixture was added to solubilize the compound. The adjuvant to compound ratio was 2:1 volume/weight. If the compound was not solubilized by the above solvent mixture, 10 ml of acetone were added. Thereafter, the solution was diluted with water to reach a total volume of 60 ml at a 2500 ppm concentration of active ingredient. The solution was then sprayed on the Calomondin trees. For each compound tested, two trees were sprayed at a 2500 ppm concentration. After 5–7 days, 5 oranges from each tree were removed and the pull force required to remove the fruit was recorded as precent reduction in pull force compared to control tree. This test procedure was only employed with Calomondin orange trees.

Three other species of oranges were also treated including Valenica, Pineapple Orange, and Parsons Brown. With respect to the latter three trees, the following abscission test was employed: Here 500 mg of the test compound was weighed into an amber, 50 ml, screw-capped bottle. 5 milliliters of dimethyl formamide were added to this to dissolve the compound. 20 ml of isopropyl alcohol containing 2 ml of Tween 20 were also added to each bottle. The bottles were then capped, labeled and sent to the orange grove for testing. There, the formulation was placed into a 1 liter Erlenmeyer flask and diluted to 500 ml with tap water. This resulted in 500 ml of a 1000 ppm active concentration. The formulation was then transferred to a Model A Sure Shot $CO_2$ powered hand sprayer. Single branches of mature orange trees of the three types set out above, having 25–50 oranges per branch, were sprayed until run off with the formulation. The branch was tagged and allowed to incubate 7 days. After 7 days the branch was inspected for evidence of activity. By clipping 15 fruit with stems attached, the force in pounds required to separate the stems from the fruit was measured with a hand force gauge. This data then allowed one to calculate the percent reduction of pull force as compared to untreated trees.

Results in the just described two procedures are set out in table IV below.

TABLE IV

| Compound Number | % Reduction Pull Force | | | |
| --- | --- | --- | --- | --- |
| | Calomondin | Valencia | Pineapple-Orange | Parsons Brown |
| 1 | 57 | — | — | — |
| 2 | 78 | >95 | — | — |
| 3 | 89 | — | 95 | — |
| 4 | 63 | — | — | — |
| 5 | 54 | — | — | — |
| 6 | 34 | — | 31 | — |
| 7 | 34 | — | 31 | — |
| 8 | 4 | — | — | — |
| 9 | 14 | — | — | — |
| 10 | 6 | — | — | 0 |
| 11 | — | — | — | — |
| 12 | 78 | 95 | — | — |
| 13 | 27 | 15 | — | — |
| 14 | — | 100 | — | — |
| 15 | — | 100 | — | — |
| 16 | 20 | — | — | — |
| 17 | — | 17 | — | — |
| 18 | — | 12 | — | — |
| 19 | — | 12 | — | — |
| 20 | 86 | — | — | — |
| 21 | — | 100 | — | — |
| 22 | — | 100 | — | — |
| 23 | — | 100 | — | — |
| 24 | — | 100 | — | — |
| 25 | 82 | — | — | — |
| 26 | — | 100 | — | — |
| 27 | — | 100 | — | — |
| 28 | — | 100 | — | — |
| 29 | — | 100 | — | — |
| 30 | — | — | — | 100 |
| 31 | — | 100 | — | — |
| 32 | — | — | — | — |
| 33 | — | 100 | — | — |
| 34 | — | 100 | — | — |
| 35 | — | — | — | — |
| 36 | — | — | — | — |
| 37 | — | — | — | — |
| 38 | 16 | — | — | — |
| 39 | — | — | — | 100 |
| 40 | 40 | — | — | — |
| 41 | 62 | — | — | — |

The compounds disclosed herein show similarly good activity when employed on such other fruits as cherries, apples, grapes, peaches, grapefruit, pears, apricots, plums, prunes, olives, tangerines, tangelos, murcotts, lemons and limes, among other fruit.

Generally, the mosts convenient method of applying a composition containing as the active ingredient one of the compounds disclosed herein to fruit-bearing plants consists of spraying the plants as described above. However, the compositions of this invention may also be applied in the form of emulsifiable concentrates, powders, granules or dusts. An agronomically acceptable carrier for the purposes of this invention includes any substance which can be used to dissolve, disperse or diffuse the chemical active ingredient, without impairing the effectiveness of the active ingredient, and which is not deleterious to the soil or the plant in any chemical or physical manner.

In formulating the compositions of this invention, other components may be included to aid in the adsorption or absorption of the active ingredient by the plant. Components such as wetting agents, solubilizers, emulsifiers, humiditants, surfactants and adjuvants are useful for this purpose and may be incorporated in the formulations.

Generally the active ingredient is employed at a concentration of up to 10,000 ppm and more often between 50 and 10,000 ppm and it is thus preferred to employ the compounds within this concentration range.

What is claimed is:
1. A 4 nitropyrazole having the formula

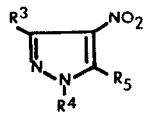

where $R^5$ is halo, $R^4$ is hydrogen and $R^3$ is alkyl.
2. The compound of claim 1 wherein $R^5$ is chloro, $R^4$ is hydrogen and $R^3$ is $C_2H_5$.
3. The compound of claim 1 where $R^5$ is chloro and $R_3$ is n-$C_3H_7$.
4. The compound of claim 1 where $R^5$ is chloro, $R^4$ is hydrogen and $R^3$ is i-$C_3H_7$.
5. The compound of claim 1 where $R^5$ is chloro, $R^4$ is hydrogen and $R^3$ is t-$C_4H_9$.
6. The compound of claim 1 where $R^5$ is chloro, $R^4$ is hydrogen and $R^3$ is C-$C_6H_{11}$.
7. The compound of claim 1 where $R^5$ is chloro, $R^4$ is hydrogen and $R^3$ is n-$C_4H_9$.
8. The compound of claim 1 where $R^5$ is bromo, $R^3$ is methyl and $R^4$ is hydrogen.

* * * * *